United States Patent [19]

Jamth

[11] Patent Number: 5,571,951
[45] Date of Patent: Nov. 5, 1996

[54] APPARATUS AND A METHOD FOR THE TESTING OF CONCRETE FOR USE WHEN CEMENTING CASINGS IN OIL AND GAS WELLS

[75] Inventor: John K. Jamth, Randaberg, Norway

[73] Assignee: Veba AS, Norway

[21] Appl. No.: 379,522

[22] PCT Filed: Aug. 7, 1992

[86] PCT No.: PCT/NO92/00128

§ 371 Date: Feb. 3, 1995

§ 102(e) Date: Feb. 3, 1995

[87] PCT Pub. No.: WO94/03803

PCT Pub. Date: Feb. 17, 1994

[51] Int. Cl.[6] .................................................. G01N 11/00
[52] U.S. Cl. .......................................... 73/54.03; 73/53.01
[58] Field of Search ................................. 73/53.01, 54.03

[56] References Cited

U.S. PATENT DOCUMENTS

| | | | |
|---|---|---|---|
| 2,966,055 | 7/1956 | Tracht et al. | 73/53.01 |
| 4,138,892 | 2/1979 | Davis . | |
| 4,259,868 | 4/1981 | Rao et al. . | |
| 4,306,395 | 12/1981 | Carpenter | 52/223 |
| 4,362,679 | 12/1982 | Malinowski | 264/82 |
| 4,425,810 | 1/1984 | Simon et al. . | |
| 4,588,443 | 5/1986 | Bache | 106/97 |
| 4,844,164 | 7/1989 | Shen | 166/291 |
| 5,021,205 | 6/1991 | Niioka | 264/69 |
| 5,035,813 | 7/1991 | Shen | 252/8.551 |
| 5,309,761 | 5/1995 | Ravi et al. | 73/151 |
| 5,361,631 | 11/1995 | Covington et al. | 73/151 |

FOREIGN PATENT DOCUMENTS

| | | |
|---|---|---|
| 1501323 | 2/1978 | United Kingdom . |
| 2061508 | 5/1981 | United Kingdom . |

*Primary Examiner*—Hezron E. Williams
*Assistant Examiner*—Jay L. Politzer
*Attorney, Agent, or Firm*—Andrus, Sceales, Starke & Sawall

[57] ABSTRACT

The invention relates to an apparatus and a method for testing concrete/cement mixtures intended for use with cementing of casings in subsea bore holes for oil and/or gas wells. The apparatus comprises a chamber (1, 1') for the accommodation of a pipe-like test container (6) for the concrete sample. The chamber (1, 1') and, consequently, the pipe-like test container (6) as well as the concrete sample may be subjected to pressure and temperature conditions substantially simulating the conditions at the intentional place of application for the cement mixture, measuring instrument means being arranged for the measurement of i.e. temperature, hydrostatic pressure and differential pressure during that part of the test which is conducted within the chamber (1, 1'). In order to establish said pressure conditions, the concrete sample within the container (6) in the chamber (1, 1') is supplied with gas, and measurements are also conducted in order to determine the magnitude of the amount of gas which has migrated into and out from the concrete sample. When the concrete sample has hardened, the pipe-like container (6) is removed from the chamber (1, 1') and the concrete sample may thereafter be subjected to further analysis.

21 Claims, 3 Drawing Sheets

APPARATUS AND A METHOD FOR THE TESTING OF CONCRETE FOR USE WHEN CEMENTING CASINGS IN OIL AND GAS WELLS

BACKGROUND OF THE INVENTION—FIELD OF THE INVENTION

This invention relates to an apparatus and a method for the testing of concrete for use when cementing casings in oil and gas wells.

BACKGROUND OF THE INVENTION—DESCRIPTION OF THE PRIOR ART

There are previously known equipment and methods for testing concrete/cement mixtures for the purpose concerned.

Thus, one known test apparatus is substantially intended to test the concrete/cement mixture with respect to micro silicon oxide content. With this known test method, a pipe having one closed end and a height of about 2 meters is filled with concrete to be tested and, above the concrete column, a water layer is placed, whereafter nitrogen gas is supplied from below. The test consists in observing the temperature development within the cement mixture or possible nitrogen gas penetration, the latter being observed through tiny gas bubbles in the water layer.

In another known test apparatus of this kind, the test parameters are the same as above, but in this case one uses a much longer pipe, about 10 meters, for the concrete/cement mixture to be tested.

Systems based on these prior art techniques suffer from a number of deficiencies and disadvantages substantially associated with the one-sidedness of the systems and of which i.a. the following may be mentioned:

Known test apparatus can not be put under pressure in order to simulate the conditions normally existing in a subsea oil or gas well. The concrete/cement mixture to be tested can not be heated, either in a static condition or during circulation and, therefore, the test can not be effected at the temperatures that are prevailing in the reservoir in which the casings are to be securely cast by means of concrete, the nature of which it is desired to test.

Likewise, it represents obvious disadvantages and deficiencies in conventional test equipment that neither hydrostatic pressure (weight of concrete plus pressure above the concrete column) nor differential pressure can be measured. One may, indeed, observe possible flow of gas through the concrete column/sample, but prior art test equipment lack measuring instruments to measure the amount of gas penetrating into or flowing out from the concrete column. Further, the concrete/cement mixture can not be circulated and, consequently, one can not simulate a complete cementing operation in situ, which, additionally, presupposes circulation of mud and separating liquid.

Also, it is desirable to test concrete/cement mixtures for cementing casings within wells drilled in permafrost and, likewise, how the concrete/cement mixture behaves itself in deviated wells and horizontal wells. Moreover, it would involve obvious advantages to be capable of logging data (data of experience) for later use. None of this is possible to realize by means of prior art concrete test methods and equipment.

SUMMARY OF THE PRESENT INVENTION

A main object of the present invention is, therefore, to provide a new apparatus and a new method of the kind defined introductorily, wherein at least most of the described disadvantages, deficiencies and limitations of conventional techniques have been completely eliminated or reduced to a substantial degree.

Thus, according to the invention, one has aimed at providing an apparatus and a method wherein concrete/cement mixtures can be tested under conditions which in many respects simulate the conditions to which the concrete/cement mixture is anticipated to be subjected in connection with the casing cementing in subsea oil or gas wells, as well as deviated wells, highly deviated wells and horizontal wells.

The main object of the invention is realized through a combination of features appearing from the following independent claims. Subordinate, advantageous features are indicated in the dependent claims.

In principle, the invention comprises an apparatus and method in which the pipe containing the concrete sample is placed in a chamber, which may have the form of two hinged chamber halves, enabling the opening and closing of the chamber. The chamber is heatable (coolable) in order to simulate the heat (cold) within a subsea well, e.g. to 100°, and may be placed under pressure, e.g. a pressure anticipated to exist in the well concerned. When this pressure has been established, one may—according to the method of the invention—add an overpressure (differential pressure), in order to simulate a gas leak from the reservoir. After the test has been performed, the chamber is opened and the concrete sample taken out for closer analysis in a laboratory. The apparatus according to the invention may be placed slopingly or horizontally, in order to simulate special conditions prevailing in deviated wells (horizontal wells).

In accordance with the invention, one may work with a pressure within the test chamber of up to 1,000 psi, and one will be capable of testing cement mixtures from −5° C. to +200°.

Hydrostatic pressure may be observed during the entire test period. Hydrostatic pressure corresponds to the weight of the cement mixture plus possible additional pressure and may be measured by means of a load cell as well as read off on a connected computer display. When the cement mixture hardens, it becomes self-supported and, then, the hydrostatic pressure descends to zero.

The added differential pressure may be adjusted from 0–15 psi with an accuracy of 0.02 psi. The magnitude of the differential pressure may be observed during the entire test.

The test equipment/method according to the invention enables one to measure how much gas possibly might have entered the cement mixture. This is important, because one then may calculate how far into the concrete column the gas has penetrated in those cases wherein the gas has not penetrated through the entire column. At the place where the gas possibly may be anticipated to penetrate, there is suitably placed a meter, in order to establish whether the penetration has been 100% or less. According to the method of the invention, one may add a certain number of milliliters of gas in order to establish a differential pressure, the concrete later being taken out for analysis.

The importance of being capable of circulating the cement mixture in accordance with the apparatus and the method of the present invention consists in that one thereby is able to simulate the course of time upon the pumping-in of the cement mixture into the bore hole. The importance of concrete testing under temperature and circulation conditions prevailing within the bore hole is i.a. associated with the shear stress (shearing) to which the concrete is subjected during pumping and which may influence the time of hardening.

In its most advanced embodiment, the new apparatus is designed and adapted to enable the performance of an entire cementing operation under simulated conditions.

Prior to the pipe being filled with concrete, one may circulate therethrough preferably oil-based mud, the various chemicals (barite, bentonite) thereof depositing along the inner wall of the pipe. Such a depositing or scale is usually called the "filter cake". Moreover, when using an oil-based mud, a grease film will form innermost along the pipe wall. As a result of this grease layer, a micro annulus may be formed, which in practice is represented through a thin oil film between the casing and concrete. This being done, one may pump in a separating liquid, in order to remove both the filter cake and the grease film. During this removal, one tests, of course, the properties of the separating liquid in relation to the mud used. It is of significant importance to remove the filter cake and the grease film so completely that the adhesion of the concrete to the casing becomes fully satisfactory. With unsatisfactory adhesion, the possibility exists that gas from e.g. a gas pocket gets the opportunity of escaping through said micro annulus between the pipe wall and adjacent cement mixture surface. During the test, one uses the same liquids (mud and separating liquid) that are to be used during the initial steps of the real cementing operation.

It may be advantageous to store all information as data of experience, in order to, on the basis these possibly updated data, improve the nature of the various cement mixtures. Examples of such important data are the period of hardening, sample temperature during the test, the amount of gas into and/or out of the sample, hydrostatic pressure and differential pressure.

These informations may be used in order to optimalize the various cement mixtures to be used for cementing casings within subsea oil and gas wells, over a very wide reservoir temperature range and under strongly differing pressure conditions. The data of experience may i.a. be used for the purpose of pure research, and in this connection it might be mentioned that gas migration in cement mixtures, especially at temperatures above 100° C., is poorly investigated.

When using a test apparatus, the construction thereof being explained later in the description, the method according to the invention comprises substantially the following working operations in succession: (i) drilling fluid is circulated through the empty concrete-accommodating container pipe until a suitable filter cake has built itself up on the inner wall of the pipe, e.g. one hour; (ii) the circulation of drilling fluid is replaced with e.g. one time circulation of separating liquid which thereby displaces the filter cake; cement is circulated in order to simulate the course of the pumping with an actual operation, in that the cement mixture may be circulated for e.g. 1–6 hours; the nature of the mixture will then be approximately such it would have been in practice, said circulation causing the cement mixture to be subjected to shear stresses, as it will be when passing through pumps, pipes, bends and the like, such that the test apparatus and method create conditions simulating the journey of the cement mixture through the drill pipe string, wherein it is subjected to shear forces through its contact with the pipe string wall, against valves and the like; (iii) whereafter the level of the cement mixture within the container pipe is adjusted such that said level becomes situated about 10 cm from the upper portion of the pipe, whereafter the concrete pumps are stopped; (iv) whereafter the test apparatus is set under pressure, e.g. 1000 psi, piping gas above and below the concrete column (which not necessarily has to be vertical but may form an arbitrary angle with a vertical axis, for testing concrete for cementing of casings in deviated wells/ horizontal wells); (v) whereafter one establishes a differential pressure in side of the container pipe, whereby that extra pressure emanating from a reservoir during real operations is simulated; a filter may be arranged to distribute the gas around the concrete sample over 360°; (vi) oil being circulated within a chamber of the apparatus in order to heat a jacket for the container pipe.

The heating oil heats the jacket for a desired time, i.e. until the cement mixture has hardened, e.g. 5–12 hours, whereafter the chamber is opened and the concrete sample taken out for analysis.

BRIEF DESCRIPTION OF THE DRAWING

An example of an embodiment of a test apparatus according to the invention is further explained in the following, reference being made to the drawings, wherein.

DESCRIPTION OF THE PREFERRED EMBODIMENT

Figure 1:
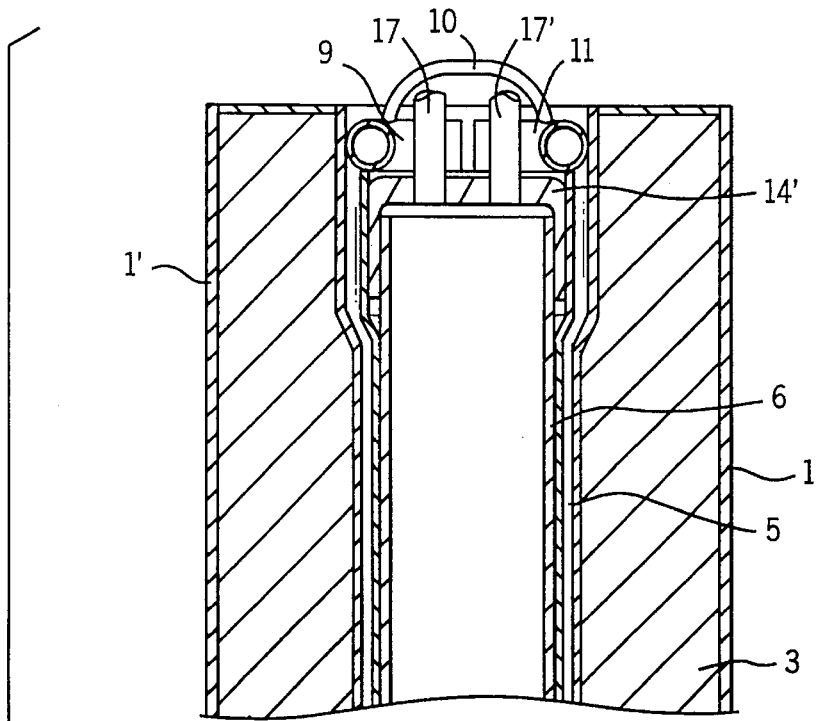
FIG. 1 shows an axial section through the test chamber with associated equipment; apparatus for circulating cement mixture, drilling fluid and separating liquid have been deleted for the sake of clarity.
Figure 2:
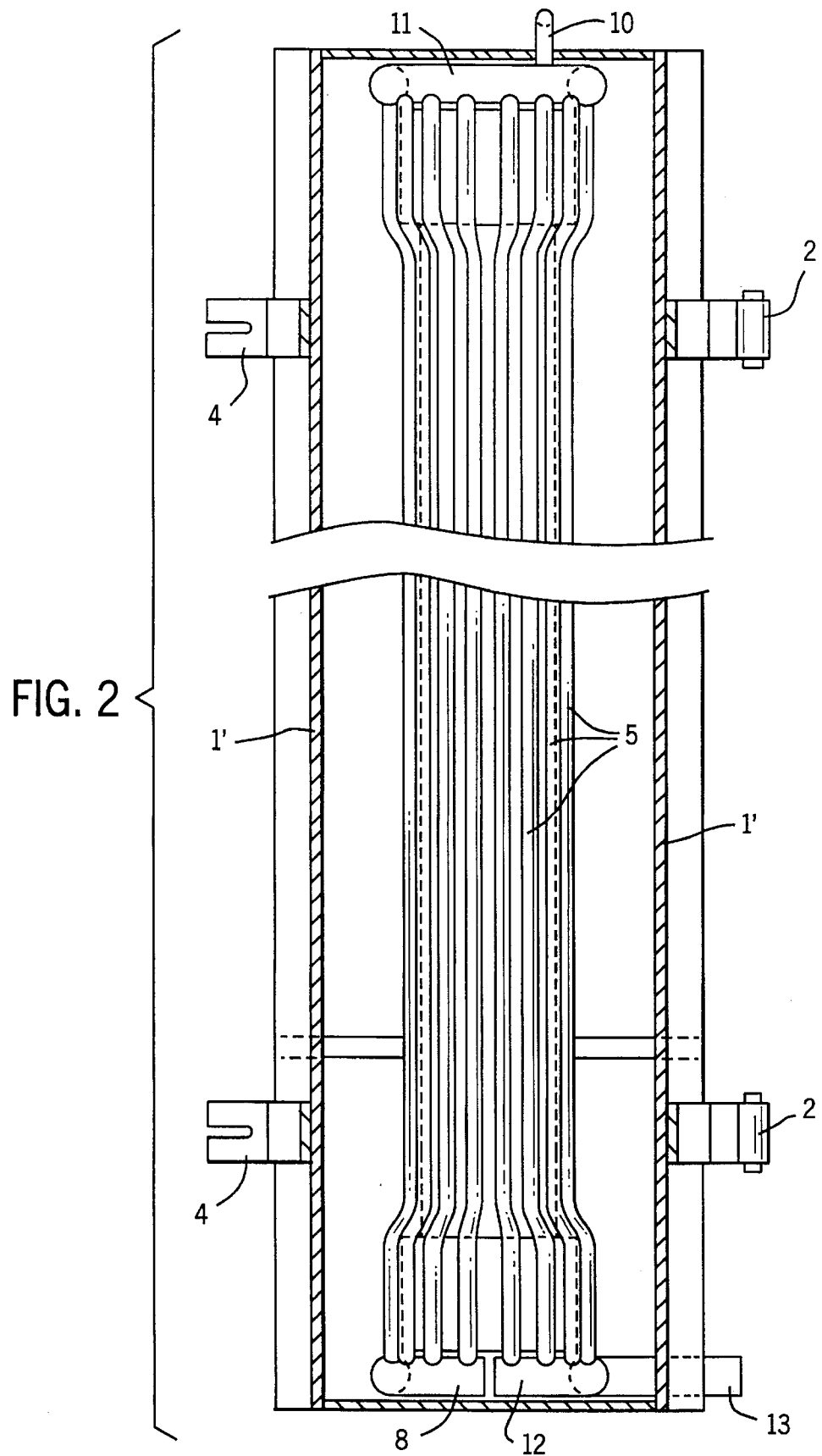
FIG. 2 shows, on the same scale as FIG. 1, a side elevational view, partly broken along the line II—II in FIG. 3.
Figure 3:
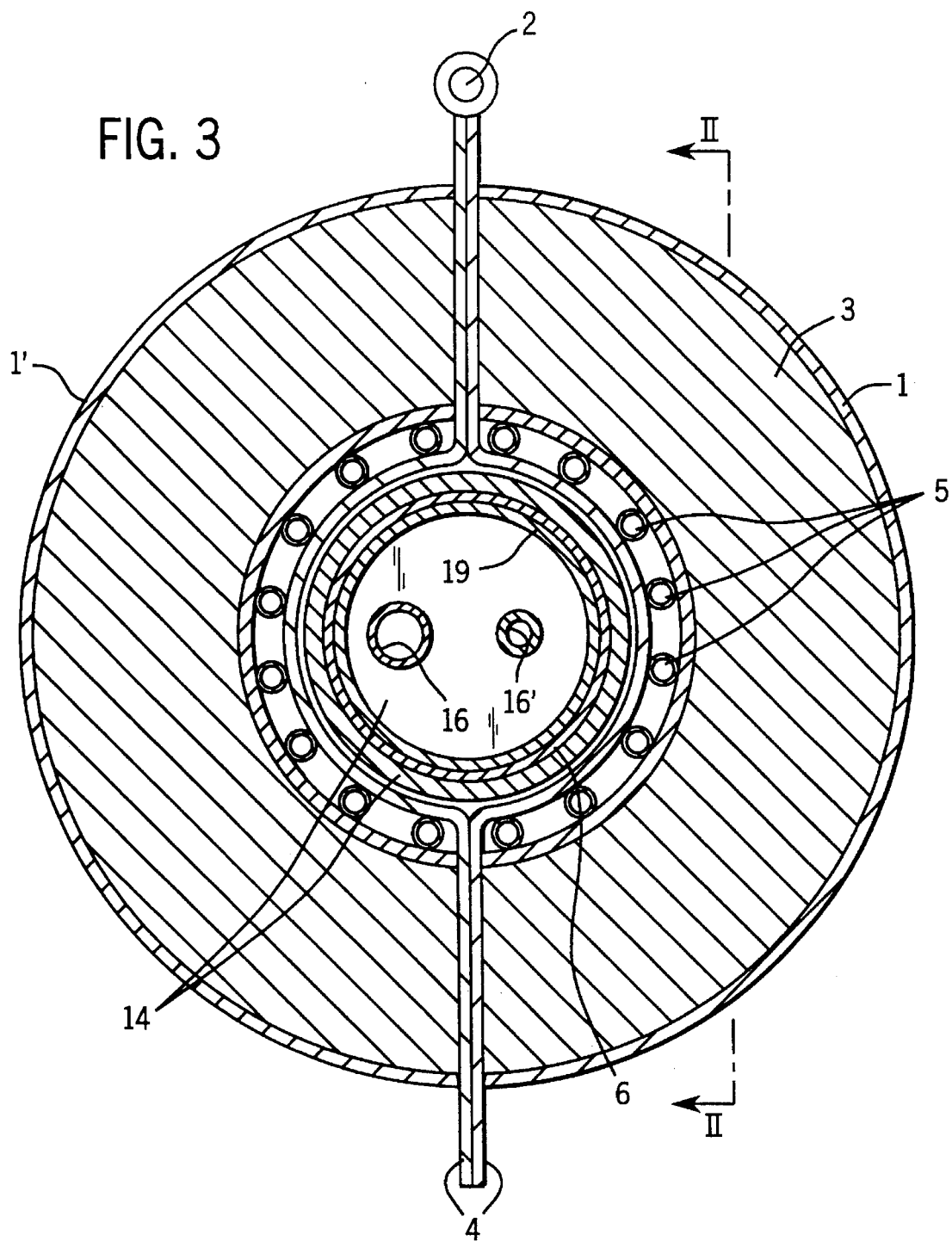
FIG. 3 shows a radial section along the line III—III in FIG. 1 on a scale approximately twice that of FIGS. 1 and 2.

In accordance with the drawings, a test chamber incorporated in an apparatus for the testing of concrete for use when cementing casings within subsea oil and gas wells comprises two half cylindrical-wall parts 1,1' interhinged by means of hinges 2 for opening and closing of the test chamber 1,1'. The chamber walls are formed as double walls, and within the spacings between the single jackets, an insulating material 3 is placed. Diametrically the hinges 2, the outer chamber jackets 1,1' are provided with cooperating coupling means 4, the engagement of which may be releasably secured by means of a locking bolt or the like, not shown.

The inner single jackets of the chamber walls are, at each axial end, bent such that the double wall, which is concentrical elsewhere, attains a somewhat smaller thickness there. Such a design is suitable i.a. for the fitting of end covers on an inner pipe to be described later on. A number of longitudinal pipes 5 are fitted within the annular spacing between the inner chamber jacket and the adjacent wall of mounting portions of the hinges 2 and the coupling means 4.

The reference numeral 6 denotes the test pipe, i.e. the pipe wherein the cement mixture to be tested is filled and subjected to heat/cold influence, pressure influence, i.a. differential pressure influence, etc., and which beforehand may be influenced through circulated drilling fluid and separating liquid, in order to investigate whether these are compatible.

The insulation 3 serves to insulate the pipes 5 against loss of heat, said pipes 5 being formed for the accommodation of circulating heat or cold medium, e.g. hot oil, in order to bring the test pipe up/down to the desired temperature, e.g. 100° C., corresponding to a rather normal reservoir temperature.

Oil or other hot heat/cold medium is pumped into and through the heating/cooling pipes 5 through a lower radially directed supply pipe 7 opening into a manifold 8 in the lower end portion of the test chamber 1,1'. The arrangement may e.g. be such that the heat/cold medium becomes pumped in through the pipe 7 and the lower manifold 8 and from there up through the pipes 5 in the left half 1' of the test chamber 1,1', in order to, at the upper end of the latter, to be transferred to an upper manifold 9, from where the heat/cold medium through a flexible hose piece 10 enters into a further manifold 11 in communication with the top ends of the pipes 5 in the right half 1 of the chamber. Then, subsequent to flowing downwards through the last-mentioned group of pipes 5, the heat/cold medium passes a further bottom manifold 12 and from there through a pipe 13 to a pump, not shown.

A flexible hose piece 10 is used in order to enable the rotation of the chamber halves 1 and 1' in relation to each other by means of the hinges 2.

Thus, when the test chamber halves 1,1' occupy the swung-open position thereof, not shown, the test pipe 6 may be placed into the chamber.

The test pipe 6 is provided with screwed-on end caps 14, 14'. In the bottom end cap 14, a load cell 15 has been placed, the load cell 15 being adapted to display the hydrostatic pressure within the test pipe/chamber.

The bottom end cap 14 of the test pipe 6 has two axially through-going bores, each associated with a pipeline/hose 16,16' constituting two inlets to the test pipe. The upper end cap 14' of the test pipe 6 is formed correspondingly, and 17 and 17' denote two outlets of the test pipe.

Now, drill mud, separating liquid and cement mixture may be circulated through the test pipe 6 through the inlet 16 and the outlet 17.

Through the inlet 16', gas is conducted in order to put the pipe 6 under pressure, and gas that might have migrated through the concrete within the test pipe 6, may be read off on a meter, not shown coupled to the outlet 17'.

Radially directed channels 18,18' extending through the double chamber wall, serve to supply gas in order to establish an overpressure (differential pressure). The reference numeral 19 denotes a filter, the task of which is to distribute this overpressure 360° around the concrete sample. Such a pressure distributing filter is not critical for the function of the invention but, nevertheless, it constitutes an advantageous feature contributing to improving the degree of accuracy of the test results.

The test apparatus according to the invention will be equipped with a temperature-indicating instrument four the temperature of the tested concrete; a measuring instrument for measuring and indication of the amount of gas into/out from the concrete sample; a pressure-indicating instrument for measuring and indication of the main pressure (i.e. pressure minus differential pressure) acting on the concrete sample, e.g. 1000 psi; a measuring instrument for the measuring of hydrostatic pressure, e.g. in the form of the load cell 15 shown; a pressure-indicating measuring instrument for the measuring and indication of differential pressure (established through gas supplied through the radial channels 18,18').

The invention claimed is:

1. An apparatus for testing a sample of a concrete/cement mixture intended for use under conditions in which the mixture is subjected to gas pressures, said apparatus enabling such testing to be carried out under pressure conditions resembling those to which the concrete/cement mixture may be subjected in use, said apparatus comprising:

chamber means for forming a tubular chamber;

an elongated, closable, tubular test container for receiving wet concrete/cement mixture to form a columnar concrete/cement mixture sample in the test container, said container having first and second, spaced ends and a side wall extending between said ends, said container being placed in said chamber of said chamber means;

first gas inlet means communicating with said test container at said first end thereof, said first gas inlet means supplying gas to said test container at said first end thereof to apply pressure to the sample in said test container;

second gas inlet means communicating with said test container at a location along the side wall of said test container that is adjacent to, but spaced from, an end of said test container, said second gas inlet means supplying gas to the exterior of the sample in said test container for establishing a differential overpressure along the columnar sample;

measuring means coupled to said test chamber for measuring the pressure to which the sample is subjected as a result of the gas supplied by said first gas inlet means;

measuring means coupled to said second end of said test chamber for measuring the amount of gas exiting from said concrete/cement mixture; and measuring means coupled to said test chamber for measuring the overpressure within said test container caused by the gas supplied through said second gas inlet means.

2. An apparatus as set forth in claim 1 wherein the columnar concrete/cement mixture sample has a central axis and wherein said first gas inlet means supplies gas to the test container to apply pressure axially to the columnar sample in said test container.

3. An apparatus as set forth in claim 1 wherein the columnar concrete/cement mixture sample has a central axis and wherein said second gas inlet means supplies gas to the exterior of the sample radially with respect to said central axis.

4. An apparatus as set forth in claim 2 wherein said second gas inlet means supplies gas to the exterior of the sample radially with respect to said central axis.

5. An apparatus as set forth in claim 3 wherein said test chamber contains means coupled to said second gas inlet means for providing the radially supplied gas about the periphery of the sample.

6. An apparatus as set forth in claim 1 wherein said second gas inlet means communicates with said test container adjacent said first end of said test container communicating with said first gas inlet means.

7. An apparatus as set forth in claim 1 further including temperature establishing means in said chamber means proximate to said test container for establishing desired temperature conditions in said test container.

8. An apparatus as set forth in claim 7 wherein said temperature establishing means comprises a plurality of pipes extending along said chamber of said chamber means to surround said test container when placed in said chamber, said pipes carrying a thermal transfer medium.

9. An apparatus as set forth in claim 1 wherein said test container contains a load cell for measuring hydrostatic pressures of the concrete/cement mixture.

10. An apparatus as set forth in claim 1 wherein said test container comprises first and second end caps mounted on said first and second ends of said test container, respectively, said first end cap having a pair of through-going bores, one of said bores of said first end cap comprising said first gas inlet means, the other bore of said first end cap comprising a passage for the concrete/cement mixture, said second end cap having a pair of through-going bores, one of said bores of said second end cap comprising a gas outlet for said test chamber, the other bore of said second end cap comprising a passage for said concrete/cement mixture, said means for measuring the amount of gas exiting said concrete/cement mixture being coupled to said one of said bores of said second end cap.

11. An apparatus as set forth in claim 1 wherein said chamber of said chamber means has a longitudinal axis, and wherein said chamber means is orientable with said longitudinal axis angularly displaced with respect to a vertical direction.

12. A method for testing a sample of a concrete/cement mixture intended for use under conditions in which the mixture is subjected to gas pressures, said method enabling such testing to be carried out under pressure conditions resembling to those to which the concrete/cement mixture is subjected in use, said method comprising the steps of:

supplying wet concrete/cement mixture to an elongated, closable tubular test container to form a columnar concrete/cement mixture sample, the columnar sample having an axis, the test container having a pair of ends;

supplying gas to one end of the test container to subject the sample in the container to a pressure simulating the general pressure conditions to which the mixture is subjected in use;

supplying additional gas to the test container at a location adjacent to, but spaced from, an end of the test container in a direction along the axis of the sample, said gas being supplied to the exterior of said sample to apply to a differential overpressure along the columnar sample;

measuring the pressure to which the sample is subjected as a result of the gas supplied to the one end of the test chamber;

measuring the amount of gas exiting the concrete/cement mixture at the other end of the test container; and measuring the overpressure within said test container caused by the additional gas supplied to the test container.

13. A method as set forth in claim 12 wherein the step of supplying gas to one end of the test container is further defined as subjecting the columnar sample to axially applied pressure.

14. A method as set forth in claim 12 wherein the step of supplying additional gas is further defined as supplying additional gas radially with respect to the axis of the columnar sample.

15. A method as set forth in claim 13 wherein the step of supplying additional gas is further defined as supplying additional gas radially with respect to the axis of the columnar sample.

16. A method as set forth in claim 4 wherein the step of supplying additional gas is further defined as providing the radially supplied gas about the periphery of the sample.

17. A method as set forth in claim 12 further defined as supplying the additional gas to the test container adjacent the end of the test container to which the gas subjecting the sample to the pressure simulating the general pressure condition is supplied.

18. A method as set forth in claim 12 further including the step of heating or cooling the concrete/cement mixture during the testing to establish desired temperature conditions in the concrete/cement mixture.

19. A method as set forth in claim 12 further defined as measuring the hydrostatic pressure of the concrete/cement mixture.

20. A method as set forth in claim 12 further defined in that, prior to the step of supplying the concrete/cement mixture to the test chamber the following steps are carried out: supplying drilling fluid to the test container to form a filter cake or grease film on a side wall of the test container; and thereafter supplying separating fluid to the test container to remove at least a portion of the filter cake and grease film.

21. A method as set forth in claim 12 further defined as regularly displacing the axis of the columnar sample with respect to a vertical direction.

* * * * *

UNITED STATES PATENT AND TRADEMARK OFFICE
CERTIFICATE OF CORRECTION

PATENT NO. :  5,571,951
DATED      :  November 5, 1996
INVENTOR(S):  Jamth

It is certified that error appears in the above-indentified patent and that said Letters Patent is hereby corrected as shown below:

CLAIM 1, Col. 8, Line 44, delete "regularly" and substitute therefor ---angularly---

Signed and Sealed this

Twenty-fifth Day of February, 1997

Attest:

BRUCE LEHMAN

*Attesting Officer*     *Commissioner of Patents and Trademarks*